US012539136B2

(12) United States Patent
Hasbun

(10) Patent No.: US 12,539,136 B2
(45) Date of Patent: Feb. 3, 2026

(54) LOW COST MULTIFUNCTIONAL MEDICAL SCISSORS

(71) Applicant: William Miguel Hasbun, Naples, FL (US)

(72) Inventor: William Miguel Hasbun, Naples, FL (US)

( * ) Notice: Subject to any disclaimer, the term of this patent is extended or adjusted under 35 U.S.C. 154(b) by 215 days.

(21) Appl. No.: 18/459,407

(22) Filed: Aug. 31, 2023

(65) Prior Publication Data

US 2024/0074781 A1 Mar. 7, 2024

Related U.S. Application Data

(60) Provisional application No. 63/374,801, filed on Sep. 7, 2022.

(51) Int. Cl.

| | |
|---|---|
| ***A61B 17/3201*** | (2006.01) |
| ***A61B 17/04*** | (2006.01) |
| ***A61B 17/076*** | (2006.01) |
| ***A61F 15/02*** | (2006.01) |

(52) U.S. Cl.

CPC ...... *A61B 17/3201* (2013.01); *A61B 17/0467* (2013.01); *A61B 17/076* (2013.01); *A61F 15/02* (2013.01)

(58) Field of Classification Search

CPC .............. A61B 17/0467; A61B 17/076; A61B 17/3201; A61B 17/29; A61B 17/2804; A61B 17/28; A61B 17/282; A61B 2017/0023; A61B 2017/00353; A61F 15/02

USPC ........................................................... 606/174

See application file for complete search history.

(56) References Cited

U.S. PATENT DOCUMENTS

| | | | | |
|---|---|---|---|---|
| 389,553 A | | 9/1888 | Diefendorf | |
| 553,579 A | | 1/1896 | Frye | |
| 4,037,276 A | | 7/1977 | Brinker | |
| 4,485,507 A | | 12/1984 | Heinz | |
| 5,219,354 A | * | 6/1993 | Choudhury ........ | A61B 17/3201 606/174 |
| 5,758,422 A | * | 6/1998 | Frank ...................... | B26B 13/10 30/260 |
| 6,647,842 B1 | | 11/2003 | Krasik-Geiger | |
| 2003/0004523 A1 | * | 1/2003 | Chan .................... | A61B 17/062 606/148 |
| 2008/0004650 A1 | * | 1/2008 | George ................... | B26B 13/06 606/174 |
| 2009/0106984 A1 | | 4/2009 | Braswell | |
| 2012/0195027 A1 | | 8/2012 | Russ et al. | |

(Continued)

*Primary Examiner* — Jocelin C Tanner

(74) *Attorney, Agent, or Firm* — LaMorte & Associates, P.C.

(57) ABSTRACT

A multipurpose medical scissor assembly having a first element and a second element arranged in a scissor configuration. The first element has a first blade support section and a first shank section. The second element has a second blade support section and a second shank section. A segment that mimics the shape of the second blade support section is mounted parallel to the second blade support section. Both the segment and the second blade support section terminate with hooked ends that create a forked configuration. The first element, the second element and the parallel segment are preferably all molded of plastic. Metal blades are attached to the first blade support section and to the second blade support section to provide cutting edges.

12 Claims, 4 Drawing Sheets

(56) References Cited

U.S. PATENT DOCUMENTS

| | | | |
|---|---|---|---|
| 2013/0046323 | A1 | 2/2013 | Whitaker |
| 2014/0352075 | A1 | 12/2014 | Stout |
| 2019/0240851 | A1 | 8/2019 | Castaneda |

* cited by examiner

LOW COST MULTIFUNCTIONAL MEDICAL SCISSORS

RELATED APPLICATIONS

This application claims the priority of U.S. Provisional Application No. 63/374,801, filed Sep. 7, 2022.

BACKGROUND OF THE INVENTION

1. Field of the Invention

In general, the present invention relates to the structure of medical scissors. More particularly, the present invention relates to medical scissors that have a low enough cost of manufacture to be considered disposable. The present invention also relates to scissors that are multifunctional and can serve purposes other than cutting, such as suture removal and staple removal.

2. Prior Art Description

Medical scissors in the form of bandage scissors, or bandage forceps, are instruments that are used by healthcare providers to cut away bandages, and other wound dressings without harming the underlying skin. Such bandage scissors typically have blunt tips so that the scissors will not cut or scrape the skin while being pressed against the skin under a bandage. Such scissors are exemplified by U.S. Patent Application Publication No. 2014/0352075 to Stout and U.S. Pat. No. 4,037,276 to Brinker.

Since bandage scissors are typically used to cut through bandages, the scissors become biologically contaminated after each use. As a consequence, in a professional healthcare facility, the scissors must either be disposed of or sterilized. Due to the very nature of scissors, scissors are difficult to make at a very low cost. Scissors for removing bandages require two long blades that are joined at a pivot joint. Accordingly, blades must be precisely ground so that they shear past one another and create a clean cutting action when the scissors are closed over various types of bandages. As a result, healthcare facilities must either pay significant sums for scissors that are thrown away after use, or they must buy expensive all-metal scissors that must undergo expensive and time-consuming autoclave procedures between uses.

When scissors are used to remove bandages or other such wound dressings, the scissors are used to access staples or sutures that are binding a wound under the bandages. Once the staples or sutures are exposed, a different medical instrument is used to remove the sutures and/or staples. This secondary instrument must also be thrown away or sterilized after each use. Since the scissors used to cut away bandages and the instruments used to remove staples and sutures are used a common wound, it would make sense to provide a multifunctional instrument that can both cut away the bandages and remove the stapes and/or sutures. However, multifunctional instruments are more complex than simple tools by nature. Accordingly, if a healthcare facility wants to use a multifunctional tool, they must either throw away the expensive instrument after each use or spend the time and money needed to properly sanitize the instrument.

A need therefore exists for a multifunctional tool that can cut way bandages and remove staples and/or sutures, wherein the multifunctional tool is very inexpensive to manufacture. In this manner, a healthcare facility can dispose of the multifunctional tool in a manner that is cost effective in relation to the costs of autoclaving such tools. This need is met by the present invention as described and claimed below.

SUMMARY OF THE INVENTION

The present invention is a multipurpose medical scissor assembly. The assembly includes a first element and a second element arranged in a scissor configuration. The first element has a first blade support section, a first shank section, and a first pivot point disposed between the first blade support section and the first shank section. Likewise, the second element has a second blade support section, a second shank section, and a second pivot point disposed between the second blade support section and the second shank section. The second pivot point is connected to said first pivot point to form a pivot joint.

A segment that mimics the shape of the second blade support section is mounted parallel to the second blade support section. The segment is held at a first distance from the second blade support section. Both the segment and the second blade support section terminate with hooked ends that create a forked configuration. The first blade support section of the first element is free to rotate to a closed position in between the segment and the second blade support section.

The first element, the second element and the parallel segment are preferably all molded of plastic. Metal blades are attached to the first blade support section and to the second blade support section to provide cutting edges.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION OF THE DRAWINGS

Although the present invention multifunction scissor assembly can be embodied in many ways, only one exemplary embodiment is illustrated. The exemplary embodiment is being shown for the purposes of explanation and description. The exemplary embodiment is selected in order to set forth one of the best modes contemplated for the invention. The illustrated embodiment, however, is merely exemplary and should not be considered as limiting when interpreting the scope of the claims.

Figure 1:
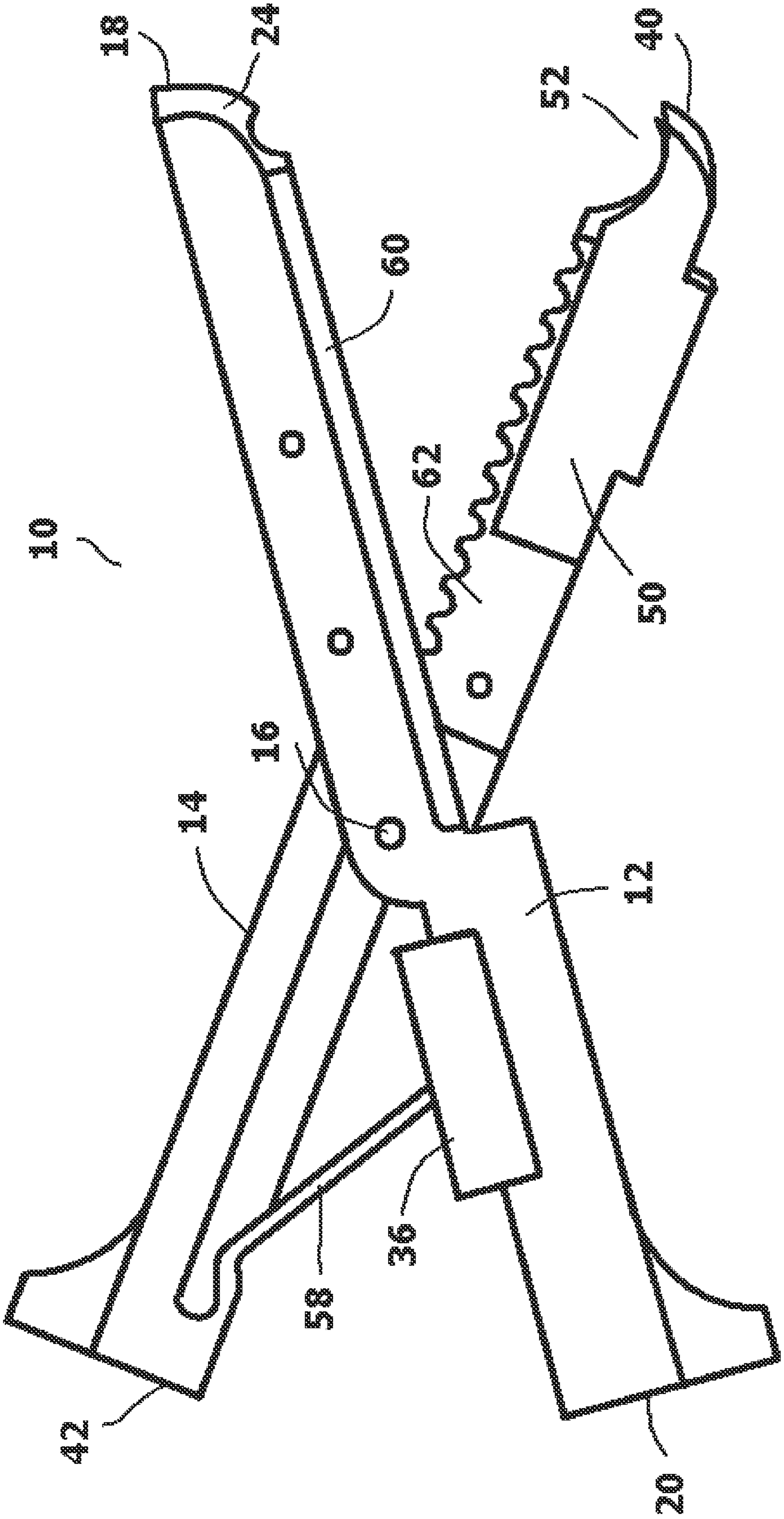
FIG. 1 is a side view of an exemplary embodiment of a scissor assembly.
Figure 2:
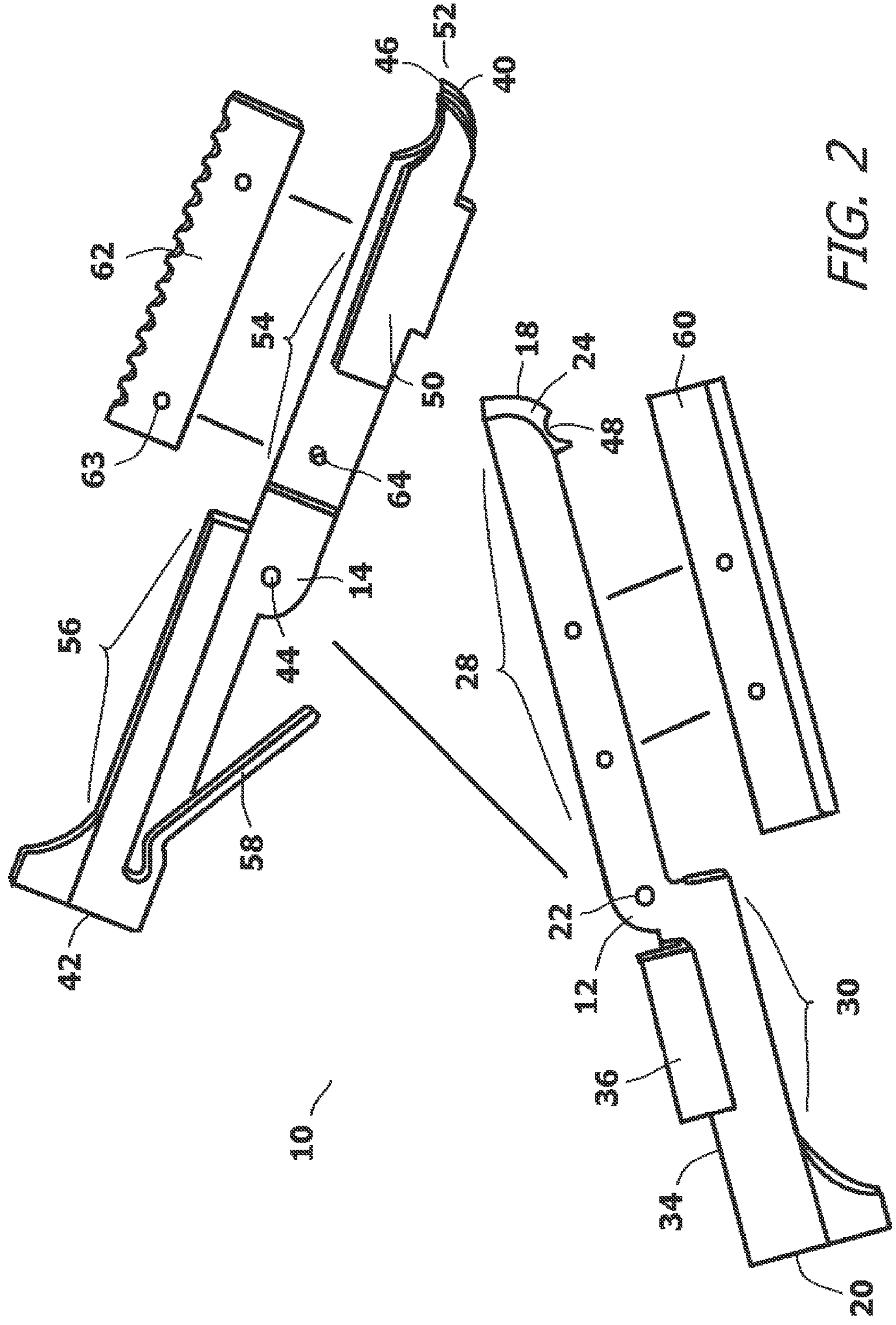
FIG. 2 is an exploded view of the exemplary embodiment of FIG. 1.
Figure 3:
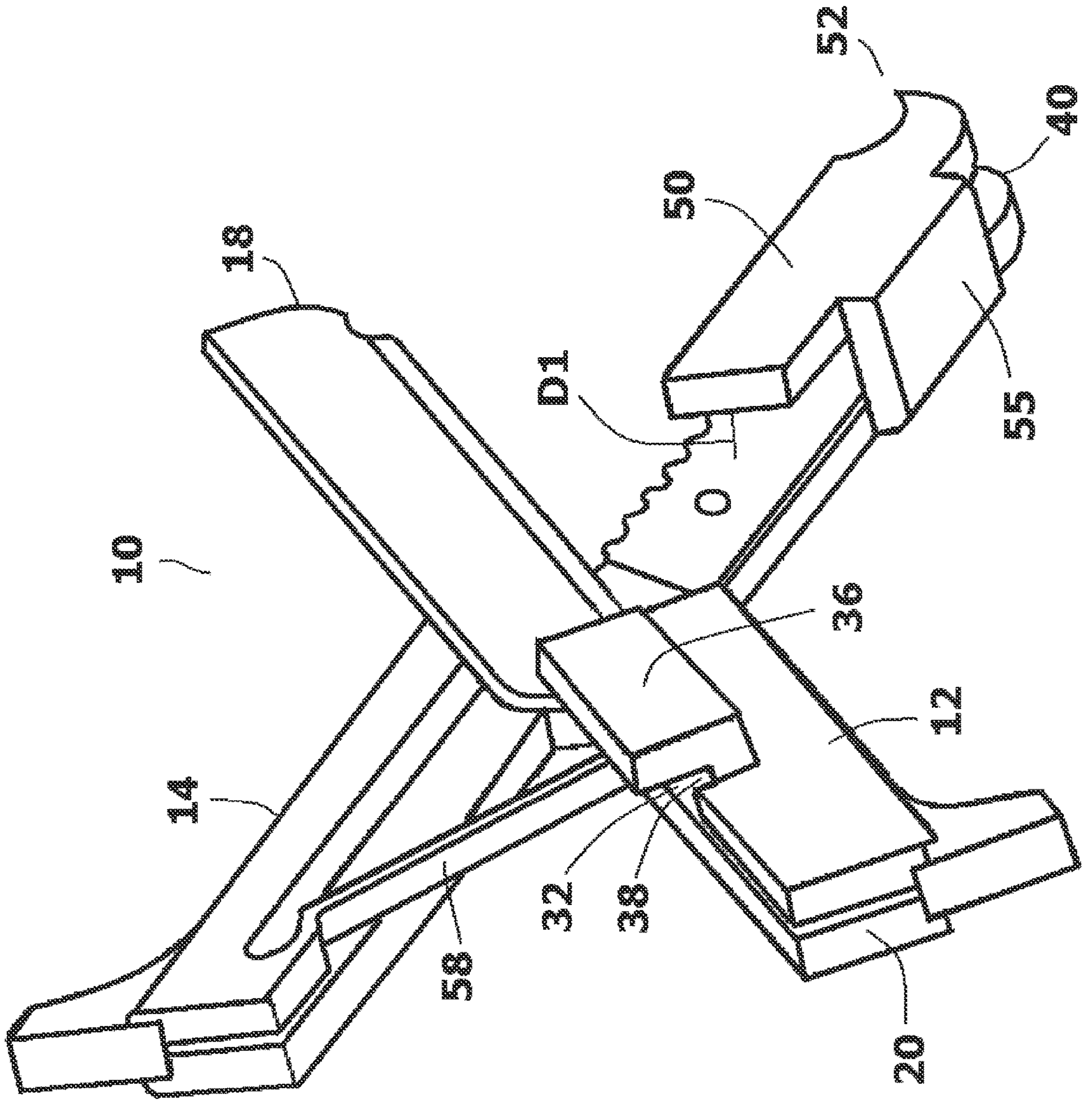
FIG. 3 shows a perspective view of the exemplary embodiment of FIG. 1.

Referring to FIG. 1, FIG. 2 and FIG. 3, a multifunction scissor assembly 10 is shown. The scissor system 10 utilizes a first element 12 and a second element 14 that are centrally joined at a pivot joint 16. The first element 12 has a first end 18, an opposite second end 20 and a first pivot point 22 that aligns with the pivot joint 16. The first end 18 terminates with a blunted edge 24. A concave depression 26 is formed in the blunted edge 24 for a purpose that is later explained.

The first element 12 has a first blade support section 28 that extends from the blunted edge 24 to the first pivot point 22. The first element 12 also has a first shank section 30 that extends from the first pivot point 22 to the second end 20. An elongated recess 32 is formed on an inner surface 34 of the first shank section 30. The elongated recess 32 is bounded by an auxiliary guide wall 36. Together, the elongated recess 32 and the auxiliary guide wall 36 define a guide slot 38. The purpose of the guide slot 38 is later described.

The second element 14 of the multifunction scissor assembly 10 has a first end 40, an opposite second end 42, and a second pivot point 44 that aligns with the pivot joint 16. The first end 40 of the second element 14 terminates with a hooked edge 46 that defines a depression 48. The second element 14 has a second blade support section 54 that extends from the hooked edge 46 to the second pivot point 44. A parallel segment 50 is attached to the second element 14 approaching the first end 40. The parallel segment 50 mimics the size and shape of the second blade support section 54 as it approaches the first end 40. The parallel segment 50 is held a distance D1 away from the second blade support section 54 by a lateral bridge 55. The second element 14 and the parallel segment 50 create a forked configuration 52, the purpose of which is later explained.

The second element 14 also has a second shank section 56 that extends from the second pivot point 44 to the second end 42. A spring arm 58 is formed as part of the second element 14. The spring arm 58 is affixed to the second shank section 56. The spring arm 58 is made of molded plastic and is preferably integrally molded as part of the second shank section 56. The spring arm 58 extends from the second shank section 56 and engages the guide slot 38 on the first shank section 30. The spring arm 58 is used to bias the scissor assembly 10 into an open configuration.

Both the first element 12 and the second element 14 are preferably molded from plastic. The only metal on the scissor assembly 10 are two blade inserts 60, 62. A first blade insert 60 attaches to the first blade support section 28 of the first element 12. Likewise, a second blade insert 62 attaches to the second blade support section 54 of the second element 14. The blade inserts 60, 62 contain mounting holes 63 that pass over mounting posts 64 that are molded into the first blade support section 28 and the second blade support section 54. The mounting posts 64 are peened by heat, therein attaching the blade inserts 60, 62 to the first blade support section 28 and the second blade support section 54. Both the first blade insert 60 and the second blade insert 62 can be straight blades. However, in the shown embodiment, the second blade insert 62 is serrated.

Figure 4:
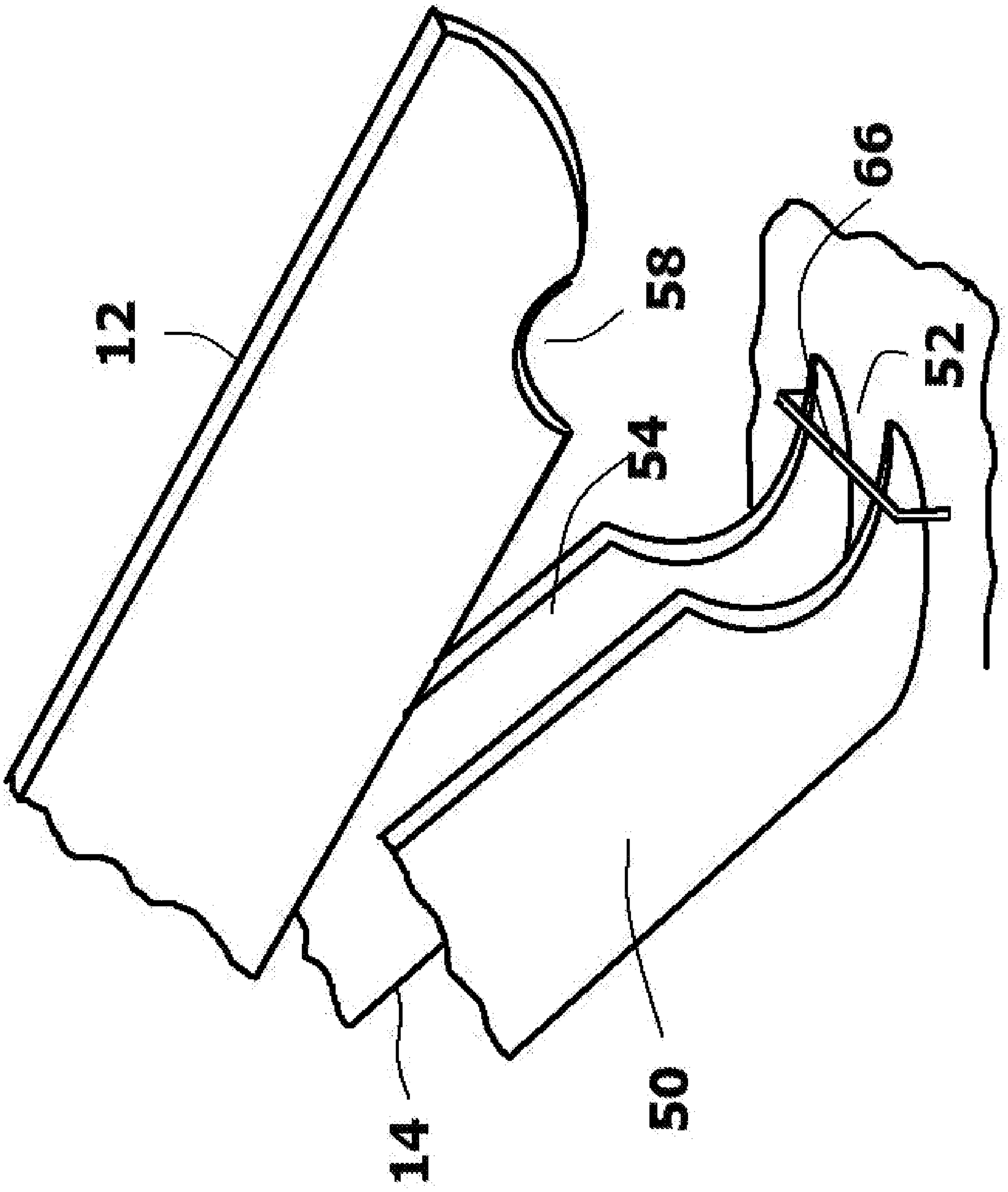
FIG. 4 shows an enlarged view of the working end of the exemplary scissor assembly being used to remove a surgical staple.

Using the scissor assembly 10, it will be understood that to cut bandages, gauze, fabric, or the like, such material is positioned between the blade inserts 60, 62 and the material is cut in the traditional manner. The first and second shank sections 30, 56 are moved toward each other, therein causing the blade inserts 60, 62 to converge and cut on the opposite side of the pivot joint 16. Referring to FIG. 4 in conjunction with FIG. 2, it can be seen that the unique terminations of the first element 12 and the second element 14 enable the scissor assembly 10 to also remove staples and sutures. In FIG. 4, a staple 66 is shown. The forked configuration 52 formed between the second blade support section 54 and the parallel segment 50 is guided under the staple 66. Once under the staple 66, the scissor assembly 10 is squeezed closed. This causes the concave depression 58 on the first element 12 to press down on the center of the staple 66 while the forked configuration 52 pulls up on either side. This action opens the staple 66 and removes the staple 66 from the wound.

Likewise, the hooked edge 46 of the second element 14 can be advanced under a suture. Once under a suture, the scissor assembly 10 can be closed, wherein the suture is cut by the converging blade inserts 60, 62.

With the exception of the blade inserts 60, 62, all components comprising the scissor assembly 10 can be molded from plastic. The first element 12 and the second element 14 are molded separately. The auxiliary guide wall 36 can be molded as part of the first element 12. Components that extend from the second element 14, such as the spring arm 58, the parallel segment 50, and the lateral bridge 55 can also be unistucturally molded as part of the second element 14. After molding, assembly includes adding the blade inserts 60, 62 and joining the first element 12 to the second element 14. The result is a very low cost and highly versatile scissor assembly 10 that can be used in place of traditional scissors as well as suture and staple forceps.

It will be understood that the embodiment of the present invention that is illustrated and described is merely exemplary and that a person skilled in the art can make many variations to that embodiment. All such embodiments are intended to be included within the scope of the present invention as defined by the claims.

What is claimed is:

1. A medical scissor assembly, comprising:

a first plastic element having a first blade support section, a first shank section, and a first pivot point disposed between said first blade support section and said first shank section;

a guide wall supported by said first shank section, wherein a guide slot is disposed between said first shank section and said guide wall;

a second plastic element having a second blade support section, a second shank section, a spring arm, and a second pivot point disposed between said second blade support section and said second shank section wherein said second pivot point is connected to said first pivot point to form a pivot joint, wherein said spring arm is integrally molded as part of said second shank section and extends from said second shank section and engages said guide slot, wherein said spring arm biases the scissor assembly into an open condition;

a segment mounted in parallel with said second blade support section at a first distance from said second blade support section, wherein said segment and said second blade support section terminate with hooked ends that create a forked configuration;

wherein said first blade support section of said first plastic element is free to rotate to a closed position in between said segment and said second blade support section.

2. The scissor assembly according to claim 1, wherein said first blade support section of said first plastic element contains a concave depression that passes between said segment and said second blade support section when in said closed position.

3. The scissor assembly according to claim 1, further including metal blades attached to said first blade support section and said second blade support section.

4. The scissor assembly according to claim 3, wherein at least one of said metal blades is serrated.

5. A medical scissor assembly, comprising:

a first plastic element having a first blade support section, a first shank section, and a first pivot point disposed between said first blade support section and said first shank section;

a guide wall supported by said first shank section, wherein a guide slot is disposed between said first shank section and said guide wall;

a second plastic element having a second blade support section, a second shank section, and a second pivot point disposed between said second blade support section and said second shank section wherein said second pivot point is connected to said first pivot point to form a pivot joint;

metal blades attached to said first blade support section and said second blade support section; and a spring arm extending from said first shank section for biasing said first blade support section and said second blade support section away from each other, wherein said spring arm is integrally molded as part of said first plastic element, and wherein said spring arm extends from said second shank section and engages said guide slot on said first shank section, wherein said spring arm biases the scissor assembly into an open condition.

6. The assembly according to claim 5, further including a segment mounted is parallel with said second blade support section at a first distance from said second blade support section, wherein said segment and said second blade support section terminate with hooked ends that create a forked configuration;

wherein said first blade support section of said first plastic element is free to rotate to a closed position in between said segment and said second blade support section.

7. The scissor assembly according to claim 6, wherein said first blade support section of said first plastic element contains a concave depression that passes between said segment and said second blade support section when in said closed position.

8. A medical scissor assembly, comprising:

a first element having a first blade support section, a first shank section, and a first pivot point disposed between said first blade support section and said first shank section;

a second element having a second blade support section, a second shank section, a spring arm molded into a single unit, said second element having a second pivot point disposed between said second blade support section and said second shank section wherein said second pivot point is connected to said first pivot point to form a pivot joint;

a guide wall supported by said first shank section, wherein a guide slot is disposed between said first shank section and said guide wall, and wherein said spring arm extends from said second shank section and engages said guide slot on said first shank section to bias the scissor assembly into an open condition;

a segment mounted in parallel with said second blade support section at a first distance from said second blade support section, wherein said segment and said second blade support section terminate with hooked ends that create a forked configuration;

wherein said first blade support section of said first element is free to rotate to a closed position in between said segment and said second blade support section.

9. The scissor assembly according to claim 8, wherein said first blade support section of said first element contains a concave depression that passes between said segment and said second blade support section when in said closed position.

10. The scissor assembly according to claim 8, wherein said segment and said second element are integrally molded as a unit from plastic.

11. The scissor assembly according to claim 8, further including metal blades attached to said first blade support section and said second blade support section.

12. The scissor assembly according to claim 11, wherein at least one of said metal blades is serrated.

* * * * *